United States Patent [19]

Scott et al.

[11] Patent Number: 4,705,686

[45] Date of Patent: Nov. 10, 1987

[54] **PROCESS FOR THE PREPARATION OF ACELLULAR *BORDETALLA PERTUSSIS* VACCINE**

[75] Inventors: Jane V. Scott, Chappaqua; Joseph F. Waggett, New City, both of N.Y.

[73] Assignee: American Cyanamid, Stamford, Conn.

[21] Appl. No.: 861,698

[22] Filed: May 9, 1986

[51] Int. Cl.[4] .......................... C12N 1/20; A61K 39/02; A61K 39/10

[52] U.S. Cl. .......................................... 424/92; 435/253; 530/825

[58] Field of Search .......................... 424/92; 530/825; 435/253

[56] References Cited

U.S. PATENT DOCUMENTS

| | | | |
|---|---|---|---|
| 3,141,824 | 7/1964 | Dahlstrom | 424/92 X |
| 3,184,394 | 5/1965 | Schmidtberger et al. | 424/92 X |
| 3,897,309 | 7/1975 | Grabner | 435/229 |
| 4,029,766 | 6/1977 | Helting | 424/92 |
| 4,234,570 | 11/1980 | Kanbayashi et al. | 530/825 X |
| 4,429,046 | 1/1984 | Lin et al. | 424/92 X |
| 4,455,297 | 6/1984 | Syukuda et al. | 424/92 |
| 4,606,919 | 8/1986 | Stojkovic et al. | 424/92 |

OTHER PUBLICATIONS

Chem-Abstracts, vol. 59, 1963, 11911a-b, Onoue et al.
Chem-Abstracts, vol. 72, 1970, 51001v, Nakase et al.
J. Bacteriol 82, 648-656, (1961), Onoue.
J. Bacteriol. 86, 648-655, (1963), Onoue.
Japan J. Microbiol. 13, 359-366, (1969), Nakase.

*Primary Examiner*—Howard E. Schain
*Attorney, Agent, or Firm*—R. P. Raymond

[57] ABSTRACT

This invention discloses a process for preparing an acellular *Bordetella pertussis* vaccine by passing culture supernatants or cellular extracts of *B. pertussis* through a column containing an ion exchange resin. The eluate from the column is detoxified and can then be employed by conventional means as a vaccine. The vaccine so produced has reduced toxicity due to the removal of endotoxin.

7 Claims, 1 Drawing Figure

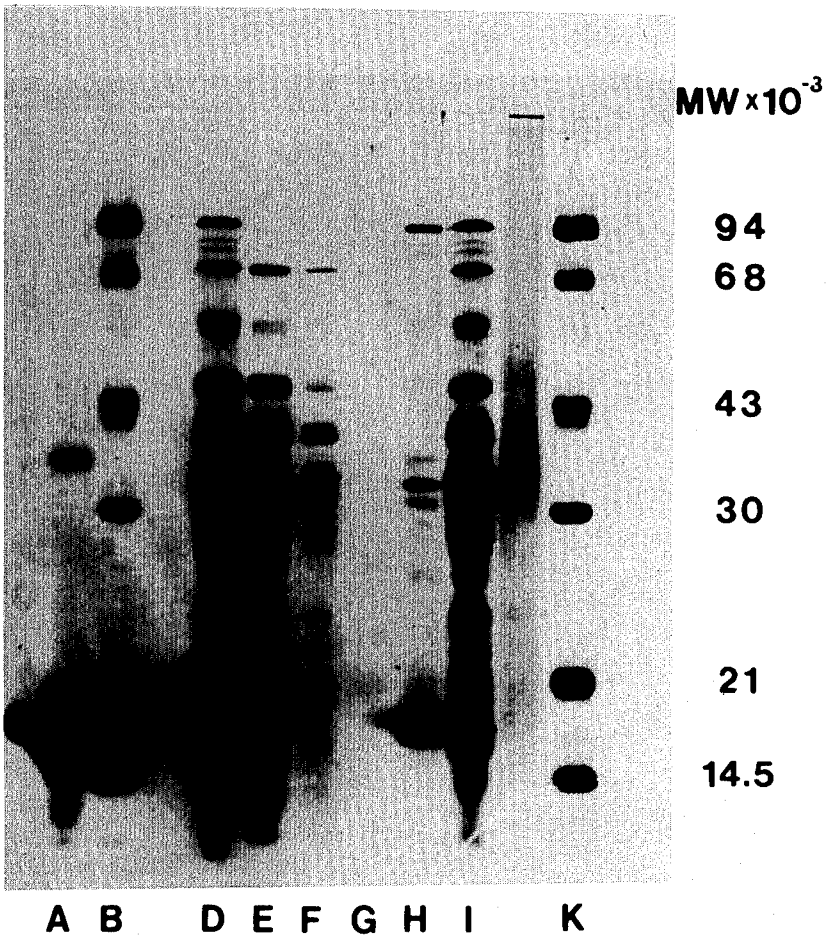
MW x10^-3
94
68
43
30
21
14.5
A B D E F G H I K

PROCESS FOR THE PREPARATION OF ACELLULAR *BORDETALLA PERTUSSIS* VACCINE

BACKGROUND OF THE INVENTION

One of the more serious diseases of infancy is whooping cough, which is an acute, highly communicable, infectious disease characterized by a paroxysmal or spasmodic cough which usually ends with a prolonged, high-pitched crowing inspiration (the whoop). In infants, choking spells may be more common than whoops. The disease is caused by the organism *Bordetella pertussis.* Immunization against this disorder has been accomplished in the past by injection of either killed-cell vaccine or extracted antigen. Until the present time, however, the available preparations, which contain a large amount of bacterial cells, have had certain shortcomings. In particular, such preparations have a tendency to produce side reactions such as fever, irritation, redness and the like.

Currently, *B. pertussis* vaccine is composed of the whole bacteria of *B. pertussis,* or of the whole bacteria and an adjuvant such as aluminum phosphate, aluminum hydroxide or a mixture thereof. A description of said vaccine production may be found in U.S. Pat. Nos. 3,577,319 and 4,429,046 and in the concurrently filed patent application of Wenlii Lin and William A. Griffith entitled: "Enhanced Large Scale Cultivation of *Bordetella Pertussis* Cells for Vaccine Production", the teachings of which are incorporated herein by reference.

Japanese Pat. No. 55-141416, entitled: "A Triple Vaccine Prepared by Adding Diphtheria Toxoid and Tetanus Toxoid to a Pertussis HA Fraction," employs the use of sucrose gradient centrifugation to remove endotoxin from Phase I *B. pertussis* hemagglutinin (HA) fraction after precipitating the culture filtrate with ammonium sulfate, then detoxifying the histamine-sensitizing factor (HSF) and leukocytosis promoting factor (LPF) in the HA fraction thus obtained. The shortcoming of this technology is its low capacity and high time consumption. Thus, it would require twenty hours to process up to 200 ml of a preparation using the largest Beckman zonal centrifuge.

U.S. Pat. No. 3,897,309 describes the removal of trace amounts of pyrogens from aqueous solutions by passing a strongly ionic solution thereof through a column of a basic anion exchange resin. The invention describes a specific process for the removal of pyrogens from L-asparaginase. When impure L-asparaginase is dissolved in a strongly ionic buffer solution and passed through a column of a basic anion exchange resin the pyrogens are selectively and irreversibly adsorbed onto the anion exchange resin while the L-asparaginase solution, free of pyrogens passes through the column. Examples of the resins cited in said patent are: Sephadex® DEAE-A-25, Sephadex® DEAE-A-50, Dowex® 1X2, Amberlite® IRA-938 and Whatman DE-52.

The chemical properties of endtoxins and proteins of different sources vary greatly, thus making it impossible for those familiar with the art to anticipate from the immediately preceding patent that a particular ion-exchange resin can separate endotoxin from the active components of *B. pertussis* vaccines. In fact, when the procedure of Example 4 in the above last cited patent was studied, using DE-52 resin, it was concluded to be inapplicable to *B. pertussis* vaccine preparation.

It is an object of the present invention to provide a *B. pertussis* vaccine of substantially improved form, having a markedly reduced tendency to produce side effects, while providing long-term immunity against whooping cough.

SUMMARY OF THE INVENTION

In the present invention, culture supernatants or cellular extracts of *B. pertussis* are passed through a column of an anion exchange resin of sufficient capacity to adsorb endotoxin and permit active, desired substances to flow through or otherwise be separated from the endtoxin. Alternatively, the supernatant or cell extract is mixed with an anion exchange resin and then the mixture is loaded into a column for elution. In addition, the present invention permits the separation of $\beta$-lactoglobulin, which may be present in the culture supernatants or cellular extracts, from the active substances. The anion exchange resin of this invention is equilibrated with 0.005M sodium phosphate buffer, pH 7.2, containing 0.05-0.1M sodium chloride. By way of example and not of limitation such anion exchange resins include Whatman DE-52 and Whatman DE-53 (Whatman Chemical Separation, Inc., 9 Bridewell Place, Clifton, N.J. 07014 U.S.A.) and Sephadex® DEAE-A-50 (Pharmacia AB, Upsala, Sweden). The active substances, including fimbrial hemagglutinin (FHA) and leucocytosis promoting toxin (LPT), also known as leucocytosis promoting factor (LPF) or pertussis toxin (PT), flow freely through the column. The effluents are then detoxified using, for example, lysine and formalin, formaldehyde or glutaraldehyde and treated with aluminum phosphate as adjuvant. These vaccine preparations are effective when tested by the specific mouse potency test based on the U.S. Standard Pertussis Vaccine.

DETAILED DESCRIPTION OF THE INVENTION

As demonstrated by the Examples hereinbelow, endotoxin is removed by the resins employed but with varying effect on the amount of active substance and, therefore, potency resulting. In a preferred embodiment of the present invention, Whatman DE-53 is employed. Whatman DE-53 yields the unexpected result of excellent separation of endotoxin with a much higher level of active substances recovered than with Whatman DE-52. This result is unanticipated since the DE-53 resin would be expected to bind much more of the active substances than DE-52, due to the nature of the resins.

The invention will be further illustrated and the methods of using the invention will be described in conjunction with the following examples which are to be taken as illustrative only and not by way of limitation.

EXAMPLE 1

The Separation of *Bordetella pertussis* Antigens from Endotoxin in a Culture Supernatant Using an Anion Exchange Resin A 10 ml amount of a *B. pertussis* culture supernatant, concentrated by ultrafiltration, in 0.005M sodium phosphate buffer, pH 7.2, containing 0.05M sodium chloride (Buffer A) was mixed with 3 g of Whatman DE-53 anion exchange resin equilibrated in Buffer A. After 2.5 hours binding at 22° C. the supernatant was aspirated and the resin was poured into a 1.5 cm×10 cm column.

The resin was washed step-wise with 15 ml volumes of 0.005M sodium phosphate buffer, pH 7.2, containing the following increasing concentrations of sodium chloride: 0.05M, 0.10M, 0.15M, 0.20M, 0.25M. Each 15 ml eluate was assayed for (a) total LPT units which equal (white blood cells count of the sample ÷ white blood cell count of the control)−1; (b) total hemagglutination (HA) units of goose red blood cells, where one unit equals the reciprocal of the last dilution causing hemagglutination; and (c) total endotoxin units determined by the Limulus ameobocyte lysate assay according to the printed procedure available from Associates of Cape Cod, Incorporated, 10 Rose Morin Drive, Falmouth, Mass., mailing address: P.O. Box 224, Woods Hole, Mass. 02543, release date Jan. 7, 1981. Under the above conditions pertussis antigens were separated from endotoxin as summarized below in Table I.

TABLE I

Separation of *Bordetella pertussis* Antigens From Endotoxin in a Culture Supernatant Using Whatman DE-53 Resin

| Fraction | NaCl Molarity | Units Total (a) LPT | Total (b) HA | Total (c) Endotoxin |
|---|---|---|---|---|
| Starting Material | 0.05 | 15,930 | 810,920 | 7,500,000 |
| Unbound Supernatant | 0.05 | *8,311 | *810,920 | *750 |
| Eluate 1 | 0.05 | *3,116 | *38,400 | *1.125 |
| Eluate 2 | 0.10 | *812 | *3,600 | *1,125 |
| Eluate 3 | 0.15 | 0 | 600 | 1,125,000 |
| Eluate 4 | 0.20 | 0 | 600 | 7,500,000 |
| Eluate 5 | 0.25 | 0 | 450 | 1,125,000 |

*Recovery of (a) LPT in unbound supernatant plus eluates 1 and 2 was 77% (12,289 units/15,930 units × 100); recovery of (b) HA in the above was 105% (854,570 units/810,920 units × 100); while (c) Endotoxin in these samples was reduced nearly 4,000 fold. Differences of less than one (1) log in the endotoxin assay results are not considered significant.

EXAMPLE 2

Endotoxin Binding on Whatman DE-53 Resin

The Whatman DE-53 resin used in Example 1 was regenerated in the 1.5 cm×10 cm column using 4 volumes of high salt wash containing 4.0M sodium chloride, 0.005M phosphate buffer, pH 7.2. Eighty ml of concentrated *B. pertussis* culture supernatant as used in Example 1 was loaded onto the resin bed. Eight fractions of 10 ml each were collected and assayed for endotoxin by the Limulus ameobocyte lysate assay to determine the capacity of the DE-53 resin to bind endotoxin. The results of this test, listed below in Table II, show that one gram of resin bound essentially $40\times10^6$ endotoxin units.

TABLE II

Endotoxin Binding Capacity of Whatman DE-53 Resin

| Fraction | Total Endotoxin Units |
|---|---|
| Starting Material | 120,000,000 |
| Eluate 1 | 150 |
| Eluate 2 | 150 |
| Eluate 3 | 600 |
| Eluate 4 | 600 |
| Eluate 5 | 1,500 |
| Eluate 6 | 1,500 |
| Eluate 7 | 15,000 |
| Eluate 8 | 150,000 |

EXAMPLE 3

The Separation of Endotoxin and Pertussis Antigens in a Cellular Extract Using an Anion Exchange Resin A cellular extract made from high salt extraction of *B. pertussis* cells were clarified and dialyzed by conventional means against a buffer consisting of 0.005M sodium phosphate, pH 7.2 containing 0.09M sodium chloride and 0.01% thimerosal (Buffer B). The sample was applied to a 5 ml column of DE-53 equilibrated in Buffer B. After washing the column in the same buffer, the resin was regenerated using 4.0M sodium chloride in 0.005M sodium phosphate buffer, pH 7.2. Table III shows the separation of endotoxin from pertussis antigens. The majority of the antigens were found to be present in Fraction 1.

TABLE III

Separation of Endotoxin and Pertussis Antigens in a Cellular Extract Using DE-53 Resin

| Fraction | Molarity NaCl | Total HA Units* | Total Endotoxin Units* |
|---|---|---|---|
| Starting Material | 0.09 | 51,200 | $7.5\times10^6$ |
| Fraction 1 | 0.09 | 30,720 | 9.0 |
| Fraction 2 | 0.09 | 1,920 | 4.5 |
| Fraction 3 | 0.09 | 960 | 45.0 |
| Fraction 4 | 0.09 | 480 | 45.0 |
| Fraction 5 | 4.00 | 640 | $3\times10^5$ |

*Determinations for hemagglutination (HA) units and endotoxin units were carried out as described in Example 1.

EXAMPLE 4

Large-scale Separation of *B. pertussis* Antigen From Endotoxin

A large scale batch of concentrated *B. pertussis* culture supernatant (8.1 L) in Buffer B was processed using 4.5 liters of packed Whatman DE-53 resin in an Amicon GA 180 column (Amicon Corporation, 21 Hartwell Avenue, Lexington, Mass. 02173) with a cross-sectional area of 254.5 cm$^2$. The resin was equilibrated in Buffer B and packed at a flow rate of 8.7 L/hour. The supernatant was loaded onto the 4.5 L column of DE-53 resin at a flow rate of 5.88 L/hour. The first 1.8 L of effluent was discarded and the remainder collected as Fraction 1. The column was washed with 1.5 L of Buffer B and the effluent added to Fraction 1. Three more washes of 1.5 L each of Buffer B were collected as Fractions 2, 3 and 4. Fractions 1–4 were assayed for *B. pertussis* antigens and endotoxin was described in Example 1. The results of these tests are shown below in Table IV.

TABLE IV

Large-scale Separation of *B. pertussis* Antigens From Endotoxin Using Whatman DE-53 Resin

| Fraction | Volume Liters | Total HA | Total Endotoxin Units |
|---|---|---|---|
| Starting Material | 8.1 | $2.6\times10^6$ | $4.9\times10^8$ |
| Fraction 1 | 8.1 | *$1.3\times10^6$ | $5.0\times10^6$ |
| Fraction 2 | 1.5 | $9.0\times10^4$ | $0.9\times10^3$ |
| Fraction 3 | 1.5 | $3.0\times10^4$ | $0.9\times10^4$ |
| Fraction 4 | 1 5 | $1.5\times10^4$ | $0.9\times10^3$ |

*The majority of the HA antigen was eluted in Fraction 1.

EXAMPLE 5

The Separation of *B. pertussis* Antigens and Endotoxin Using Whatman DE-52 Anion Exchange Resin Anion exchange resin Whatman DE-52 was substituted for Whatman DE-53 anion exchange resin and the procedure of Example 1 was followed. Although the separation of *B. pertussis* antigens and endotoxin was similar to that obtained in Example 1, the recovery of antigens were considerably lower as shown below in Table V.

TABLE V

Separation of *B. pertussis* Anitgens and Endotoxin Using Whatman DE-52 Resin

| Fraction | NaCl (molarity) | Total HA* | Total Endotoxin Units* |
|---|---|---|---|
| Starting Material | 0.05 | 810,920 | 7,500,000 |
| Unbound Supernatant | 0.05 | 102,400 | 75 |
| Eluate 1 | 0.05 | 7,200 | 112.5 |
| Eluate 2 | 0.10 | 3,600 | 1,125,000 |
| Eluate 3 | 0.15 | 1,800 | 1,125,000 |
| Eluate 4 | 0.20 | 600 | 1,125,000 |
| Eluate 5 | 0.25 | 150 | 112,500 |

*Determinations for hemagglutination (HA) units and endotoxin units were carried out as described in Example 1.

EXAMPLE 6

The Separation of *B. pertussis* Antigens and Endotoxin Using Sephadex ® DEAE-A-50 Anion Exchange Resin A 10 ml bed volume of Sephadex ® DEAE-A-50 anion exchange resin (Pharmacia), equilibrated in Buffer A was mixed with 25 ml of the same concentrated *B. pertussis* culture supernatant used in Example 1. After adsorption and elution from a 2.5 cm diameter column following the procedure of Example 1, the pertussis antigens and endotoxin were separated as shown in Table VI.

TABLE VI

Separation of Pertussis Antigens and Endotoxin Using Sephadex ® DEAE-A-50

| Fraction | NaCl (molarity) | Total HA* | Total Endotoxin Units* |
|---|---|---|---|
| Starting Material | 0.05 | 96,000 | 37,500,000 |
| Eluate 1 | 0.05 | 9,600 | 300 |
| Eluate 2 | 0.10 | 1,600 | 3,000 |
| Eluate 3 | 0.15 | 800 | 30,000 |
| Eluate 4 | 0.20 | 800 | 300,000 |
| Eluate 5 | 0.25 | 400 | 3,000,000 |

*Determinations for hemagglutination (HA) units and endotoxin units were carried out as described in Example 1.

EXAMPLE 7

Preparation of a Component Vaccine

The acellular *B. pertussis* material obtained from Fraction 1 in Example 4 was concentrated using 50% saturated ammonium sulfate precipitation. The resuspended pellet was detoxified using formalin and lysine according to procedures well known to those skilled in the art. After dialysis to remove excess formalin, the material was stored at 4°–8° C. The soluble vaccine was adsorbed to aluminum phosphate before combining with diphtheria and tetanus adsorbed toxoids. Pertussis potency of the adsorbed vaccine thus obtained was 11.85 units/total immunizing dose (TID) based upon the standard U.S. dosage of 1.5 ml.

EXAMPLE 8

The Separation of Endotoxin and β-lactoglobulin from *B. pertussis* Antigens A 10 ml aliquot of concentrated *B. pertussis* culture supernatant in Buffer B containing 0.1% β-lactoglobulin was passed through a 5 ml bed volume of DE-53 equilibrated in Buffer B. The column was washed with Buffer B and then regenerated with 4M NaCl, 0.005M phosphate buffer, pH 7.2. Under these conditions the column had the capacity to separate both endotoxin and β-lactoglobulin from pertussis antigens. Endotoxin and β-lactoglobulin which bound to the DE-53 resin were removed by the high salt regeneration step. See Table VII and FIG. 1 below. Table VII provides comparative separation data which resulted from the hereinabove described procedure.

TABLE VII

Separation of Endotoxin and β-lactoglobulin From Pertussis Antigens

| Fraction | NaCl Molarity | Total HA* | Total Endotoxin Units* |
|---|---|---|---|
| Starting Material | 0.09 | 80 | $7.5 \times 10^5$ |
| Fraction 1 | 0.09 | 80 | $7.9 \times 10^1$ |
| Fraction 2 | 0.09 | 0 | $7.5 \times 10^1$ |
| Fraction 3 | 0.09 | 0 | $<1.0 \times 10^1$ |
| Fraction 4 | 4.00 | 0 | $>7.5 \times 10^5$ |

*Determinations for HA units and endotoxin units were carried out as described in Example 1.

FIG. 1 is a photograph of a 0.2% sodium dodecyl sulfate-10% polyacrylamide gel run according to Laemmli, U.K., *Nature,* 227:680 (1970) depicting the effect of column chromatography on an acellular *B. pertussis* sample containing 0.1% β-lactoglobulin while using Whatman DE-53 as the anion exchange resin as described in Example 8. In particular, Lane A is 0.1% β-lactoglobulin; Lanes B and K are molecular weight makers; Lane D is acellular pertussis containing 0.1% β-lactoglobulin; Lane E is Fraction 1 from the DE-53 column; Lane F is Fraction 2 from the DE-53 column; Lane G is Fraction 3 from the DE-53 column; Lane H is Fraction 4 from the DE-53 column; and Lane I is acellular pertussis without β-lactoglobulin.

The procedures described in the preceding Examples were carried out under the customary aseptic conditions and the final material in each case was uncontaminated by undesired organisms. The Examples do, in fact, demonstrate that endotoxin is removed from concentrated *B. pertussis* culture supernatants or cellular extracts when column chromatography with an anion exchange resin equilibrated with a neutral phosphate buffer of a low salt concentration is employed. The procedures also demonstrates that certain anion exchange resins are more preferred than others. In conclusion, vaccines produced by incorporating the process procedures described by the present invention constitute improved products due to the removal of some of the impurities which tend to produce side effects upon injection into mammals.

We claim:

1. A process for the preparation of an acellular *Bordetella pertussi* vaccine which comprises:

(a) mixing in the presence of a neutral buffer solution of low ionic strength comprising about 0.005M sodium phosphate, pH 7.2, and about 0.05 to about 0.1M sodium chloride and about 0.01% thimerosal an extract of *B. pertussis* cells or the supernatant of a *B. pertussis* culture with an anion exchange resin selected from the group consisting of Whatman DE-52, Whatman DE-53 and SEPHADEX® DEAE-A-50;

(b) loading the mixture into a column;

(c) eluting the column; and (d) detoxifying the eluate.

2. A process for the preparation of an acellular *Bordetella pertussis* vaccine which comprises:

(a) loading an extract of *B. pertussis* cells or the supernatant of a *B. pertussis* culture onto an ion-exchange column comprising an anion exchange resin where the resin in such column is selected from the group consisting of Whatman DE-52, Whatman DE-53 and SEPHADEX DEAE-A-50, and the resin is equilibrated with a neutral buffer solution of low ionic strength comprising about 0.005M sodium phosphate, pH 7.2, and about 0.05 to about 0.1M sodium chloride and about 0.01% thimerosal;

(b) eluting the column; and (c) detoxifying the eluate.

3. The process according to claim 1 or 2 wherein the anion exchange resin is Whatman DE-53.

4. An acellular *Bordetella pertussis* vaccine composition prepared according to the process of claim 1 or 2.

5. An acellular *Bordetella pertussis* vaccine composition prepared according to the process of claim 3.

6. A component vaccine which comprises an acellular *Bordetella pertussis* component, prepared according to the process of claim 1 or 2, adsorbed to aluminum phosphate; diphtheria adsorbed toxoid; and tetanus adsorbed toxid.

7. A component vaccine which comprises an acellular *Bordetella pertussis* component, prepared according to the process of claim 3, adsorbed to aluminum phosphate; diphtheria adsorbed toxoid; and tetanus adsorbed toxoid.

* * * * *